United States Patent
Leigh (10) Patent No.: US 9,516,433 B2
(45) Date of Patent: Dec. 6, 2016

(54) COMBINED FUNCTIONAL COMPONENT AND IMPLANTABLE ACTUATOR POSITIONING MECHANISM

(75) Inventor: C. Roger Leigh, East Ryde (AU)

(73) Assignee: Cochlear Limited, Macquarie University, NSW (AU)

( * ) Notice: Subject to any disclaimer, the term of this patent is extended or adjusted under 35 U.S.C. 154(b) by 260 days.

(21) Appl. No.: 13/403,690

(22) Filed: Feb. 23, 2012

(65) Prior Publication Data

US 2013/0225912 A1 Aug. 29, 2013

(51) Int. Cl.
*H04R 25/00* (2006.01)
*A61F 2/18* (2006.01)

(52) U.S. Cl.
CPC ....... *H04R 25/606* (2013.01); *A61F 2002/183* (2013.01)

(58) Field of Classification Search
CPC ...... H04R 25/00; H04R 25/02; H04R 25/60; H04R 25/604; H04R 25/606; H04R 25/608; H04R 25/65; A61N 1/36032; A61F 11/04

USPC .......... 600/25; 607/57; 623/10, 24
See application file for complete search history.

(56) References Cited

U.S. PATENT DOCUMENTS

| | | | |
|---|---|---|---|
| 2002/0038072 A1* | 3/2002 | Muller | H04R 25/606 600/25 |
| 2004/0010181 A1* | 1/2004 | Feeley | H04R 25/608 600/25 |
| 2008/0188707 A1* | 8/2008 | Bernard et al. | 600/25 |
| 2009/0124849 A1* | 5/2009 | Pergola | 600/25 |
| 2010/0010569 A1* | 1/2010 | Parker et al. | 607/57 |
| 2012/0078368 A1* | 3/2012 | Lenarz | A61F 2/18 623/10 |

* cited by examiner

*Primary Examiner* — Charles A Marmor, II
*Assistant Examiner* — Thaddeus Cox
(74) *Attorney, Agent, or Firm* — Hauptman Ham, LLP (57) ABSTRACT

An implantable component including an implantable body including a functional component of the implantable medical device, and implantable actuator positioning mechanism connected to and extending from the implantable body, the actuator positioning mechanism configured to removably receive an implantable actuator.

33 Claims, 10 Drawing Sheets

COMBINED FUNCTIONAL COMPONENT AND IMPLANTABLE ACTUATOR POSITIONING MECHANISM

BACKGROUND

1. Field of the Invention

The present invention relates generally to a prostheses, and more particularly, to an implantable actuator positioning mechanism of a hearing prosthesis combined to a functional component of the hearing prosthesis.

2. Related Art

Hearing loss is generally of two types, conductive and sensorineural. Sensorineural hearing loss is due to the absence or destruction of the cochlear hair cells which transduce sound into nerve impulses. Various hearing prostheses have been developed to provide individuals suffering from sensorineural hearing loss with the ability to perceive sound. For example, cochlear implants have an electrode assembly which is implanted in the cochlea. In operation, electrical stimuli are delivered to the auditory nerve via the electrode assembly, thereby bypassing the inoperative hair cells to cause a hearing percept.

Conductive hearing loss occurs when the natural mechanical pathways that provide sound in the form of mechanical energy to cochlea are impeded, for example, by damage to the ossicular chain or ear canal. For a variety of reasons, such individuals are typically not candidates for a cochlear implant. Rather, individuals suffering from conductive hearing loss typically receive an acoustic hearing aid. Hearing aids rely on principles of air conduction to transmit acoustic signals to the cochlea. In particular, hearing aids amplify received sound and transmit the amplified sound into the ear canal. This amplified sound reaches the cochlea in the form of mechanical energy, causing motion of the perilymph and stimulation of the auditory nerve.

Unfortunately, not all individuals suffering from conductive hearing loss are able to derive suitable benefit from hearing aids. For example, some individuals are prone to chronic inflammation or infection of the ear canal. Other individuals have malformed or absent outer ear and/or ear canals resulting from a birth defect, or as a result of medical conditions such as Treacher Collins syndrome or Microtia.

For these and other individuals, another type of hearing prosthesis has been developed in recent years. This hearing prosthesis, commonly referred to as a middle ear implant, converts received sound into a mechanical force that is applied to the ossicular chain or directly to the cochlea via an actuator implanted in or adjacent to the middle ear cavity.

SUMMARY

Some aspects of the present invention are generally directed to an implantable component, comprising an implantable body including a functional component of the implantable medical device, and an implantable actuator positioning mechanism connected to and extending from the implantable body, the actuator positioning mechanism configured to removably receive an implantable actuator.

Some other aspects of the present invention are generally directed to an implantable component, comprising an implantable actuator positioning mechanism configured to receive an implantable actuator, wherein the implantable actuator positioning mechanism is configured to be fixedly attached to a functional component of a hearing prosthesis.

Some other aspects of the present invention are generally directed to a method of implanting an implantable component of a middle ear hearing prosthesis including a functional component and a middle ear implant actuator, comprising obtaining access to a mastoid region beneath skin of a human head, fixing the implantable component to the mastoid bone at a location corresponding to at least one of an outer face of the mastoid bone or a location proximate the outer face of the mastoid bone, wherein the action of fixing the implantable component secures both the functional component and the middle ear implant actuator to the mastoid bone.

Some other aspects of the present invention are generally directed to a middle ear implant, comprising a receiver-stimulator, and a middle ear implant actuator, wherein the middle ear implant is configured to hold the actuator at an adjustably fixed location relative to the receiver-stimulator.

BRIEF DESCRIPTION OF THE DRAWINGS

Embodiments of the present invention are described below with reference to the attached drawings, in which.

DETAILED DESCRIPTION

Aspects of the present invention are generally directed to an implantable component of a middle ear hearing prosthesis that comprises an implantable housing containing a receiver-stimulator of the hearing prosthesis. A middle ear actuator is operationally coupled to the receiver-stimulator, and an actuator positioning mechanism is connected to and extends from the implantable housing. The middle ear actuator is received in and supported by the actuator positioning mechanism, and is configured to position the received actuator at an adjustably fixed location relative to the implantable housing. In an exemplary embodiment, the just-described implantable component may be handled by a surgeon as a single component during implantation of the implantable component, and may be secured to a mastoid region of a recipient via fixation of the implantable component at an outer face of a mastoid bone of the mastoid region.

While some of the embodiments detailed herein are directed towards hearing prosthesis in general and middle ear implants in particular, other embodiments include an actuator positioning mechanism usable as detailed herein and variations thereof that is attached to a functional component of any type of implant that utilizes an actuator.

Figure 1:
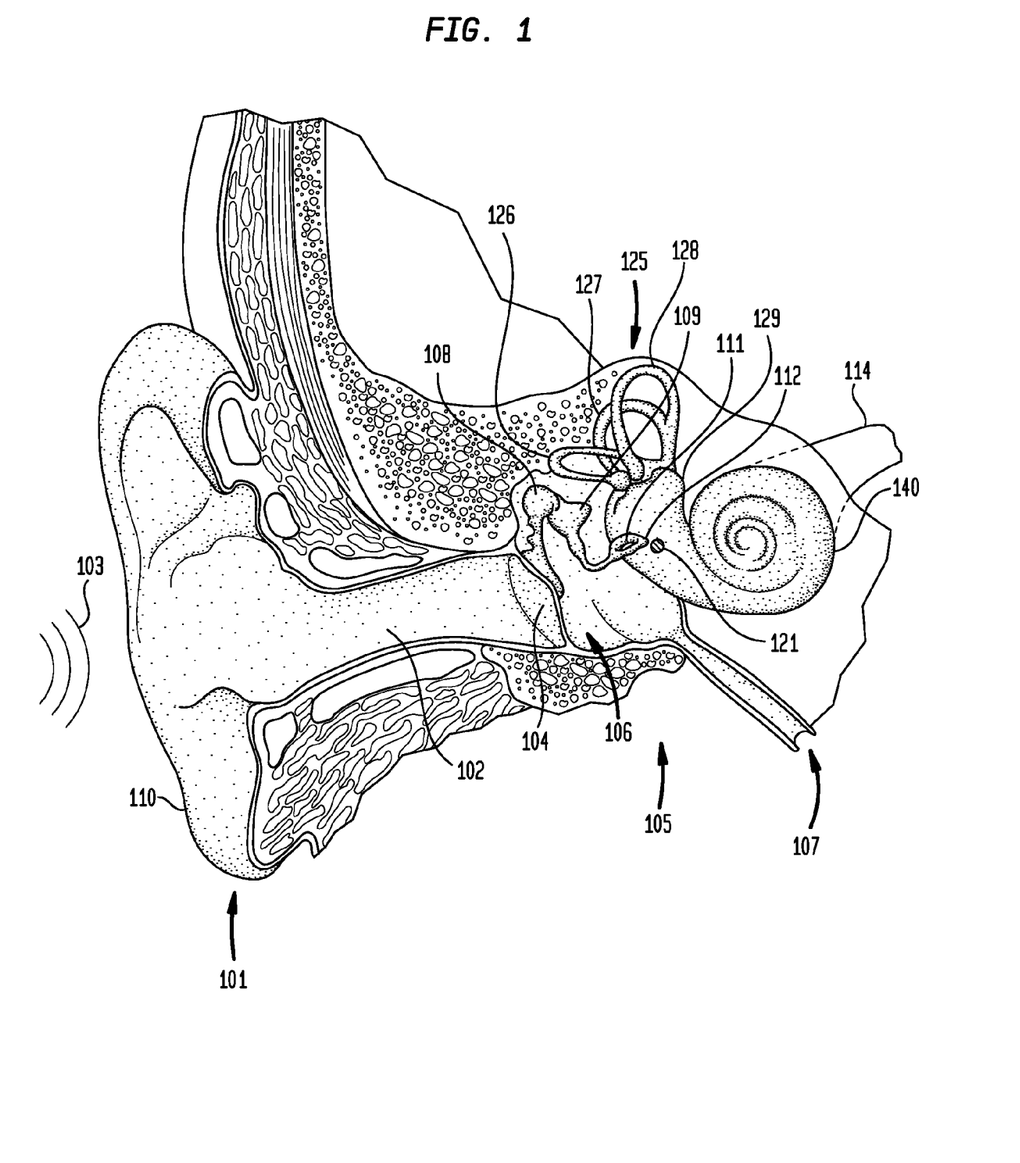
FIG. 1 is perspective view of a human ear.

FIG. 1 is a perspective view of a human skull showing the anatomy of the human ear. As shown in FIG. 1, the human ear comprises an outer ear 101, a middle ear 105 and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121. This vibration is coupled through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to the vibration of tympanic membrane 104. This vibration sets up waves of fluid motion of the perilymph within cochlea 140. Such fluid motion, in turn, activates hair cells (not shown) inside cochlea 140. Activation of the hair cells causes nerve impulses to be generated and transferred through the spiral ganglion cells (not shown) and auditory nerve 114 to the brain (also not shown) where they cause a hearing percept.

As shown in FIG. 1, semicircular canals 125 are three half-circular, interconnected tubes located adjacent cochlea 140. Vestibule 129 provides fluid communication between semicircular canals 125 and cochlea 140. The three canals are the horizontal semicircular canal 126, the posterior semicircular canal 127, and the superior semicircular canal 128. The canals 126, 127 and 128 are aligned approximately orthogonally to one another. Specifically, horizontal canal 126 is aligned roughly horizontally in the head, while the superior 128 and posterior canals 127 are aligned roughly at a 45 degree angle to a vertical through the center of the individual's head.

Each canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

Figure 2A:
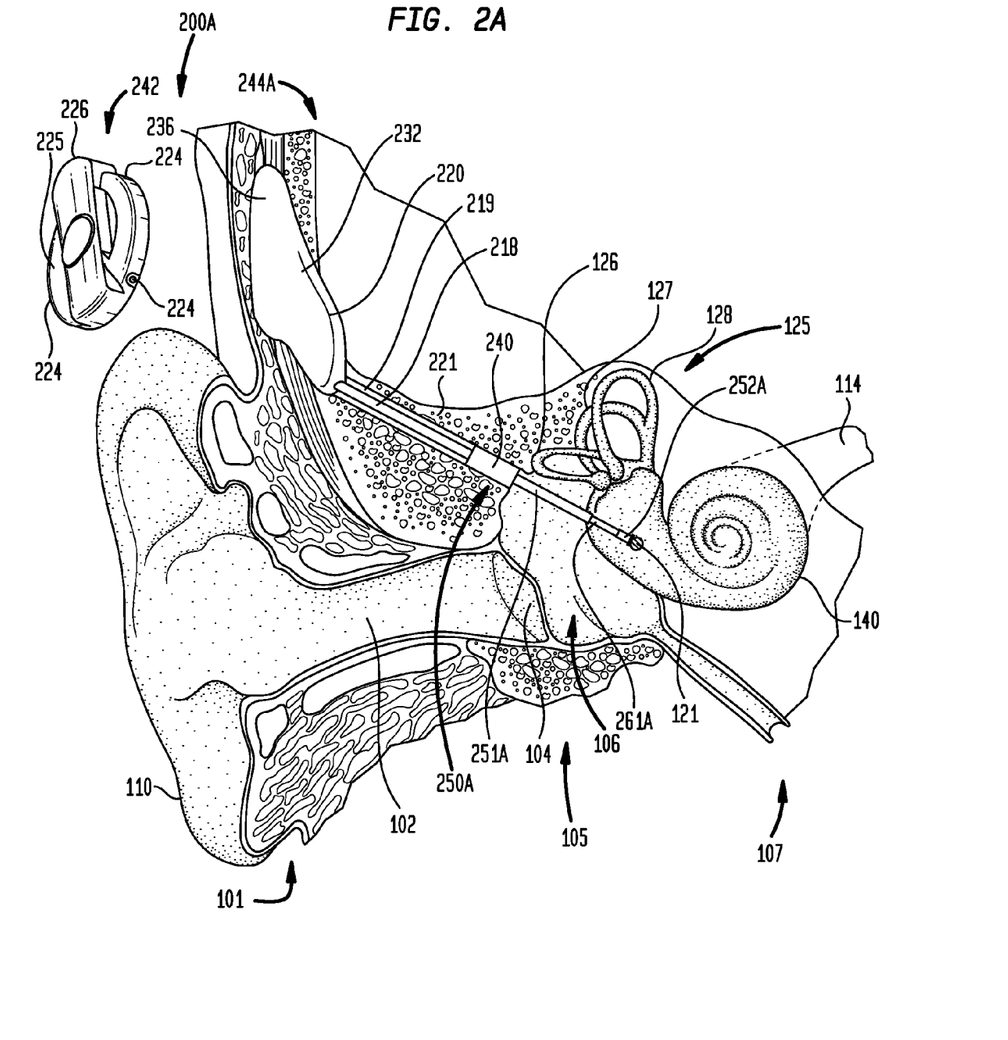
FIG. 2A is a perspective view of an exemplary middle ear implant.

FIG. 2A is a perspective view of an exemplary direct acoustic cochlear stimulator 200A in accordance with embodiments of the present invention. Direct acoustic cochlear stimulator 200A comprises an external component 242 that is directly or indirectly attached to the body of the recipient, and an internal component 244A that is temporarily or permanently implanted in the recipient. External component 242 typically comprises two or more sound input elements, such as microphones 224, for detecting sound, a sound processing unit 226, a power source (not shown), and an external transmitter unit 225. External transmitter unit 225 comprises an external coil (not shown). Sound processing unit 226 processes the output of microphones 224 and generates encoded data signals which are provided to external transmitter unit 225. For ease of illustration, sound processing unit 226 is shown detached from the recipient.

Internal component 244A comprises an internal receiver unit 232, a stimulator unit 220, and a stimulation arrangement 250A in electrical communication with stimulator unit 220 via cable 218 extending through artificial passageway 219 in mastoid bone 221. Internal receiver unit 232 and stimulator unit 220 are hermetically sealed within a biocompatible housing, and are sometimes collectively referred to as a stimulator/receiver unit.

Internal receiver unit 232 comprises an internal coil (not shown), and optionally, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated platinum or gold wire. The electrical insulation of the internal coil is provided by a flexible silicone molding (not shown). In use, implantable receiver unit 232 is positioned in a recess of the temporal bone adjacent auricle 110.

In the illustrative embodiment of FIG. 2A, ossicles 106 have been explanted. However, it should be appreciated that stimulation arrangement 250A may be implanted without disturbing ossicles 106.

Stimulation arrangement 250A comprises an actuator 240, a stapes prosthesis 252A and a coupling element 251A which includes an artificial incus 261B. Actuator 240 is osseointegrated to mastoid bone 221, or more particularly, to the interior of artificial passageway 219 formed in mastoid bone 221.

In this embodiment, stimulation arrangement 250A is implanted and/or configured such that a portion of stapes prosthesis 252A abuts an opening in one of the semicircular canals 125. For example, in the illustrative embodiment, stapes prosthesis 252A abuts an opening in horizontal semicircular canal 126. In alternative embodiments, stimulation arrangement 250A is implanted such that stapes prosthesis 252A abuts an opening in posterior semicircular canal 127 or superior semicircular canal 128.

As noted above, a sound signal is received by microphone(s) 224, processed by sound processing unit 226, and transmitted as encoded data signals to internal receiver 232. Based on these received signals, stimulator unit 220 generates drive signals which cause actuation of actuator 240. The mechanical motion of actuator 240 is transferred to stapes prosthesis 252A such that a wave of fluid motion is generated in horizontal semicircular canal 126. Because vestibule 129 provides fluid communication between the semicircular canals 125 and the median canal, the wave of fluid motion continues into the median canal, thereby activating the hair cells of the organ of Corti. Activation of the hair cells causes appropriate nerve impulses to be generated and transferred through the spiral ganglion cells (not shown) and auditory nerve 114 to cause a hearing percept in the brain.

Figure 2B:
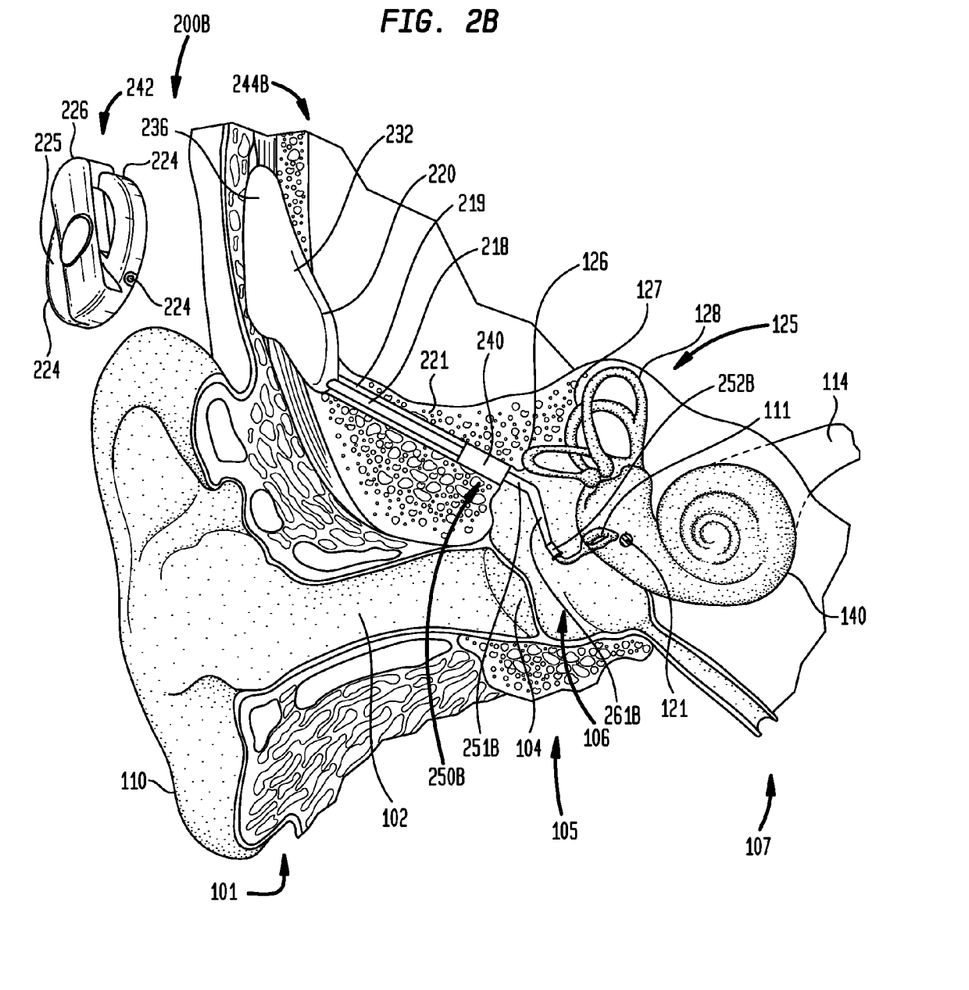
FIG. 2B is a perspective view of an alternate embodiment of an exemplary middle ear implant.

FIG. 2B depicts an exemplary embodiment of a middle ear implant 200B having a stimulation arrangement 250B comprising actuator 240 and a coupling element 251B. Coupling element 251B includes a stapes prosthesis 252B and an artificial incus 261B which couples the actuator to the stapes prosthesis. In this embodiment, stapes prosthesis 252C abuts stapes 111.

Figure 3:
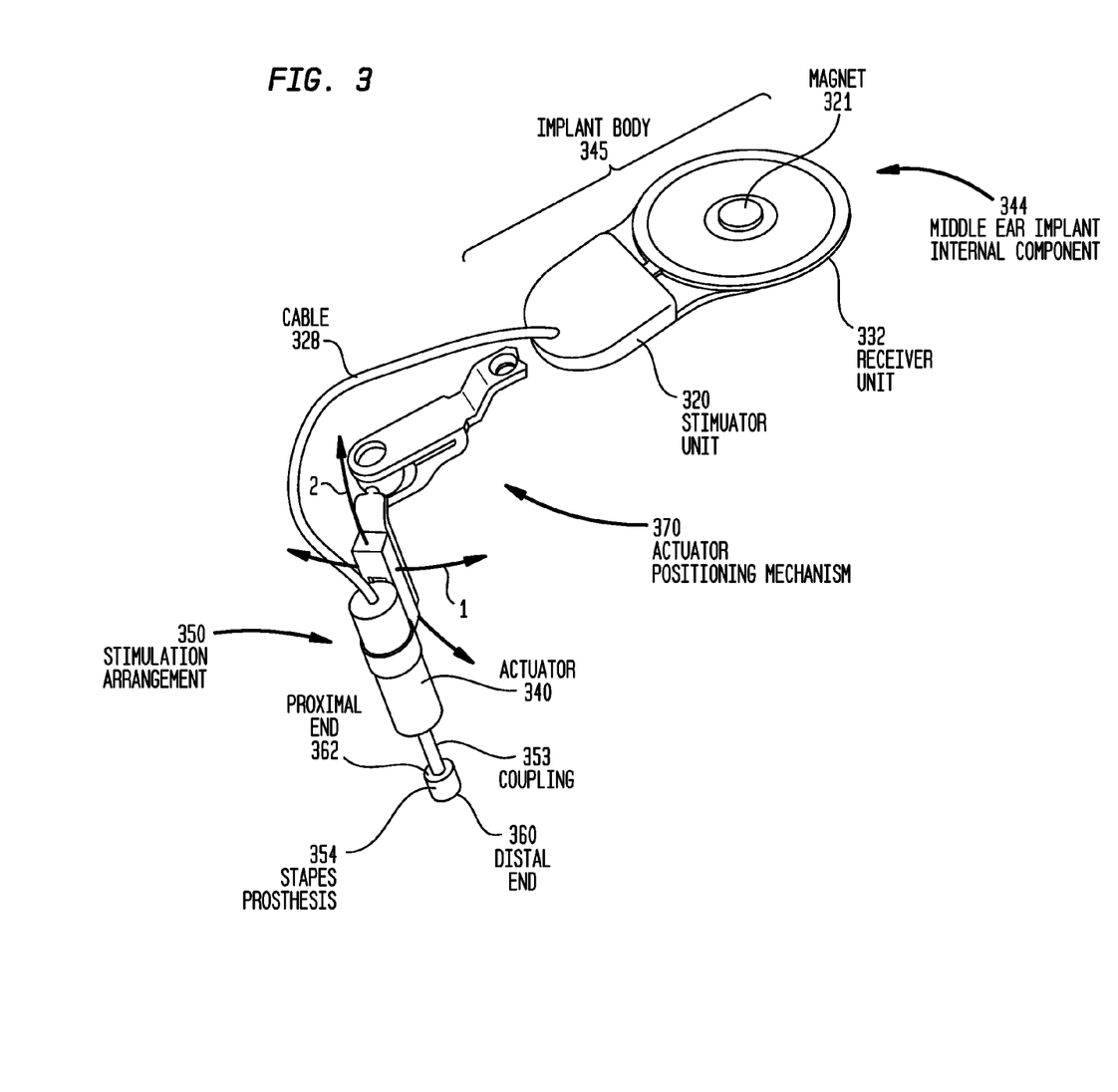
FIG. 3 is a schematic depicting an exemplary implantable component in accordance with an embodiment of the present invention.

FIG. 3 is a perspective view of an exemplary internal component 344 of a middle ear implant according to an exemplary embodiment of the present invention. Internal component 344 comprises an internal receiver unit 332, a stimulator unit 320, a stimulation arrangement 350, and an actuator positioning mechanism 370. As shown, receiver unit 332 comprises an internal coil (not shown), and in some embodiments, a magnet 321 fixed relative to the internal coil. Internal receiver unit 332 and stimulator unit 320 are typically hermetically sealed within a biocompatible housing. This housing has been omitted from FIG. 3 for ease of illustration, and hence the end of the actuator positioning mechanism 370, discussed in more detail below, which connects to the housing, is depicted with broken lines. This connection will be described with respect to later FIGS. Collectively, the internal receiver unit 332, the stimulator unit 320 and the housing form an implant body 345.

Stimulator unit 320 is connected to stimulation arrangement 350 via a cable 328. Stimulation arrangement 350 comprises an actuator 340, a stapes prosthesis 354 and a coupling element 353. A distal end of stapes prosthesis 354 is configured to be positioned in one or more of the configurations noted above with respect to FIGS. 2A-2B. A proximal end of stapes prosthesis 354 is connected to actuator 340 via coupling element 353 and the distal end of the prosthesis is directly or indirectly coupled to the cochlea. In operation, actuator 340 vibrates stapes prosthesis 354. The vibration of stapes prosthesis 354 generates waves of fluid motion of the perilymph, thereby activating the hair cells of the organ of Corti. Activation of the hair cells causes appropriate nerve impulses to be generated and transferred through the spiral ganglion cells and auditory nerve 114.

Middle ear implant internal component 344 further includes actuator positioning mechanism 370. As may be seen, actuator positioning mechanism 370 is connected to and extends from implantable body 345 and is configured to removably receive actuator 340.

Figure 4:
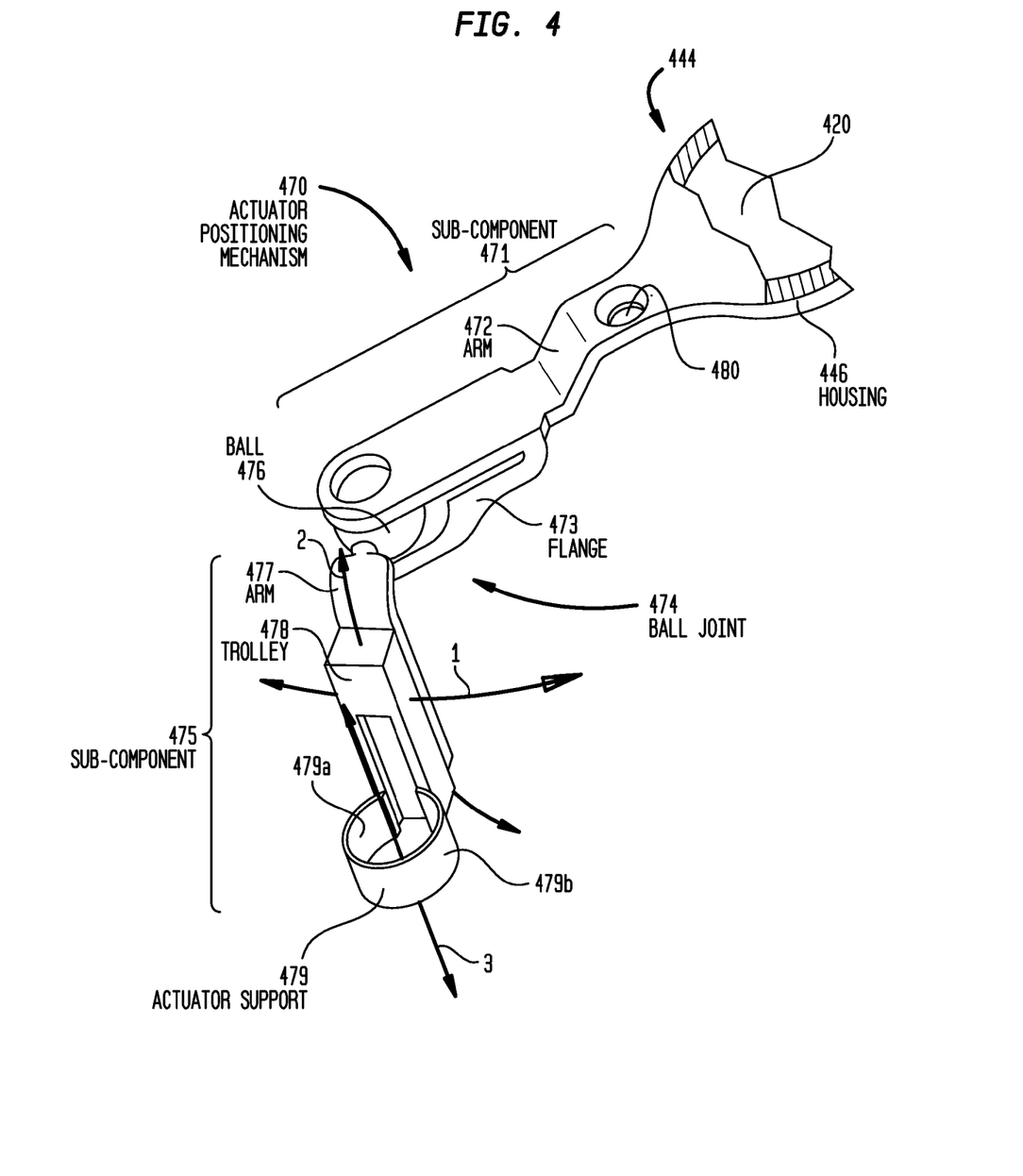
FIG. 4 is a perspective view depicting additional details of the exemplary implantable component of FIG. 3.

Additional details of the middle ear implant internal component 344 in general, and the actuator positioning mechanism 370 in particular, will now be described with respect to FIG. 4, where middle ear implant internal component 444 corresponds to middle ear implant internal component 344 of FIG. 3, actuator positioning mechanism 470 corresponds to actuator positioning mechanism 370 of FIG. 3, and stimulator unit 420 corresponds to stimulator unit 320 of FIG. 3. In FIG. 4, the stimulation arrangement 350 has been removed for clarity, although it will be understood that cable 328 extends from housing 446, which hermetically seals stimulator 420 (and the receiver, which is not shown), via a feedthrough or an orifice therein.

FIG. 4 depicts actuator positioning mechanism 470 as comprising two sub-components: extension arm 471 and extension arm 475. Sub-component 471 includes arm 472 which is an integral part of housing 446 (where the cross-hatching of housing 446 seen in FIG. 4 corresponds to the wall of the housing, as will be described in greater detail below). In an exemplary embodiment, arm 472 may be part of the same casting forming at least part of housing 446 (i.e., the arm 472 and at least a portion of the housing 446 form a monolithic component), although in an alternate exemplary embodiment, arm 472 may be a separate component that is attached to the housing 446 (e.g., via laser welding). In an exemplary embodiment, the casting may be made partially or totally out of titanium. In this regard, it is noted that the actuator support mechanism may be made partially or totally out of titanium, and the housing 446 may be made out of a different material. Sub-component 471 also includes flange 473 which forms a female portion of ball joint 474. In this regard, sub-component 475 includes the male portion of the ball joint 474, in the form of a ball 476, as may be seen. Ball joint 474 permits the ball 476 of sub-component 475 to move within the female portion, thereby permitting sub-component 475 to articulate relative to sub-component 471, and thus permitting actuator 340 to likewise articulate relative to middle ear implant internal component 344.

Ball joint 474 enables the actuator 340 to be positioned at an adjustably fixed location relative to the implantable body 345. In an exemplary embodiment, the ball joint 474 permits the location of the actuator 340 to be adjustable relative to the implant body in two degrees of freedom, represented by arrows 1 and 2 (first and second degrees of freedom, respectively), in FIGS. 3 and 4, although in some embodiments the joint may permit the location of the actuator 340 to be adjustable relative to the implant body in only one degree of freedom or in more than two degrees of freedom.

While actuator positioning mechanism 470 is depicted with a ball joint 474, other types of joints may be utilized. By way of example, the joint may comprise a malleable portion of a structural component of the actuator positioning mechanism 470 that permits the actuator 340 to be positioned as just detailed or variations thereof. In an exemplary embodiment, the joint is an elastically deformable portion or plastically deformable portion or is a combination of elastically deformable and plastically deformable portions so as to enable the adjustment of the location of the received actuator relative to the implant body in the at least one degree of freedom.

As noted above, actuator positioning mechanism 470 further includes sub-component 475. Sub-component 475 comprises ball 476 of ball joint 474, arm 477, trolley 478 and actuator support 479. Actuator support 479 is depicted as being in the form of a collar, and receives and otherwise holds actuator 340 therein, and thus holds the actuator 340 to the actuator positioning mechanism 470.

The collar has an exterior surface 479a and an interior surface 479b, configured to receive actuator 340. The interior diameter of the collar, formed by interior surface 479b is approximately the same as the outer diameter of the cylindrical body of actuator 340. The outer diameter of the collar, formed by exterior surface 479a, is sized such that the collar will fit into the artificial passageway 219. The length of the collar is shorter than the cylindrical body of the actuator 340, but in other embodiments, it may be the same length or about the same length or longer.

As noted, actuator support 479 and actuator 340 are configured to enable the actuator 340 to be removably secured to the actuator support 479, and thus the actuator positioning mechanism 470. This removable securement may be, in some embodiments, sufficient to prevent actuator 340 from substantially moving from the retained location in the actuator support 479, and the actuator positioning mechanism 470 is configured to prevent the actuator support 479 from substantially moving within the artificial passageway 219 during operation of the actuator 340. For example, the removable securement may be achieved via an interlock between the actuator 340 and the collar that provides retention sufficient to withstand reaction forces resulting from operation of actuator 340.

In an exemplary embodiment, the interlock is provided by an interference fit between inner surface 479a of the collar of actuator support 479 and an outer surface of actuator 340. In an alternate embodiment, the interlock is implemented as threads of inner surface 479a that interface with corresponding threads on the outer surface of actuator 340. In another embodiment, O-rings or the like may be used to snuggly wrap around actuator 340 and snuggly fit inside the collar of actuator support 479. Grooves on the actuator 340 and/or on the collar may be included to receive the O-ring. In other embodiments, compression of the O-ring between the actuator 340 and the collar provides sufficient friction to retain the components in the actuator support 479. In another embodiment, actuator support 479 or actuator 340 includes a biased extension that is adjusted against the bias to insert the actuator into the support. The extension may engage a detent on the opposing surface to interlock the actuator and the support. Other embodiments include protrusions and corresponding channels on opposing surfaces of the actuator and support. An exemplary embodiment includes a spring-loaded detent that interfaces with a detent receiver of the opposing surface to hold the actuator in the support or that extends behind the actuator once the actuator has been positioned beyond the detent. An alternate embodiment may utilize O-rings to interlock the actuator in the support. Adhesive may be used to interlock the actuator in the support. Any device, system or method that will interlock actuator in the support that will permit embodiments detailed herein and/or variations thereof to be practiced may be utilized in some embodiments.

The trolley 478, which is rigidly connected to actuator support 479, is configured to move linearly in the direction of arrow 3 parallel to the longitudinal direction of extension of arm 477. In this exemplary embodiment, arm 477 includes tracks with which trolley 478 interfaces to retain trolley 478 to arm 477. These tracks also to establish trolley 478 and arm 477 as a telescopic component configured to enable the adjustment of the location of actuator support 479, and thus actuator 340 when received therein, relative to the housing 446 (thus the implant body), in at least one degree of freedom (i.e., the degree of freedom represented by arrow 3). It is noted that other embodiments may permit adjustment in at least two or at least three degrees of freedom. Thus, when the trolley component is combined with the aforementioned joint 474, the actuator positioning system enables the location of the actuator 340 to be adjustable relative to the implant body in at least two or at least three degrees of freedom.

Movement of the trolley 478 along arm 477 may be accomplished via a jack screw mechanism where the jack screw is turned via a screw driver or a hex-head wrench. Movement of the trolley 478 may also or alternatively be achieved via application of a force thereto that overcomes friction between the trolley 478 and the arm 477. Any device, system or method that permits trolley 478 to move relative to arm 477 may be used in some embodiments detailed herein and variations thereof.

Figure 5A:
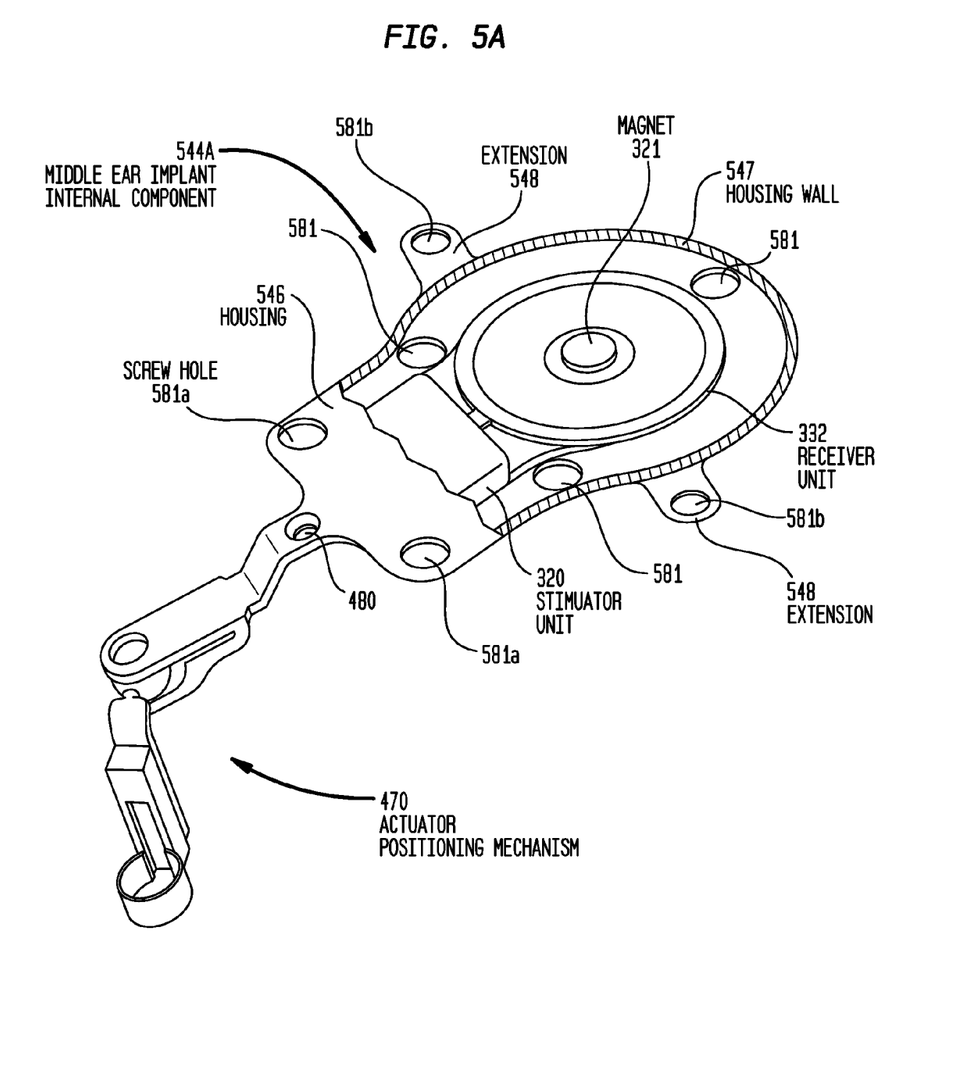
FIG. 5A depicts some details of an exemplary alternate embodiment of the exemplary implantable component of FIG. 3.

Referring to FIGS. 3 and 4, it may be seen that arm 472 of actuator positioning mechanism 470 includes screw hole 480. Screw hole 480 is configured to receive a bone screw (not shown in FIGS. 3 and 4, but shown in FIG. 5B discussed below). The utility of such a bone screw is discussed below. While screw hole 480 is depicted as being located on (in) arm 472, in other embodiments, screw holes may be located elsewhere on the middle ear implant internal component (and bone screws may be received therein). In this regard. FIG. 5A depicts an exemplary middle ear implant internal component 544A, which in some embodiments functionally corresponds to one or more or all of the middle ear implant internal components detailed herein and variations thereof, that includes a housing 546 in which a plurality of screw holes 571 are located. As may be seen, the screw holes 581 are located to avoid the functional components contained in the housing 546, such as the receiver unit 332 and the stimulator unit 320. In an exemplary embodiment, more or fewer screw holes 581 may be included in the middle ear implant internal component 544A.

As may be seen, FIG. 5A depicts only a portion of housing 546, the absent portion being absent to permit depiction of the internal functional components. As may be seen, a number of screw holes 581 are located within housing wall 547. Such screw holes 581 may be formed via cylindrical structures that extend from the top of the housing to the bottom of the housing, thereby enabling the hermetic seal of the housing to be maintained. Screw holes 581 may also be formed in extensions of the housing that extend outboard of the housing wall. Such may be the case with screw holes 581. It is noted that these extensions may be present elsewhere about the housing 546, as is depicted by way of example in FIG. 5A via extension 548, which includes screw holes 581b.

Figure 5B:
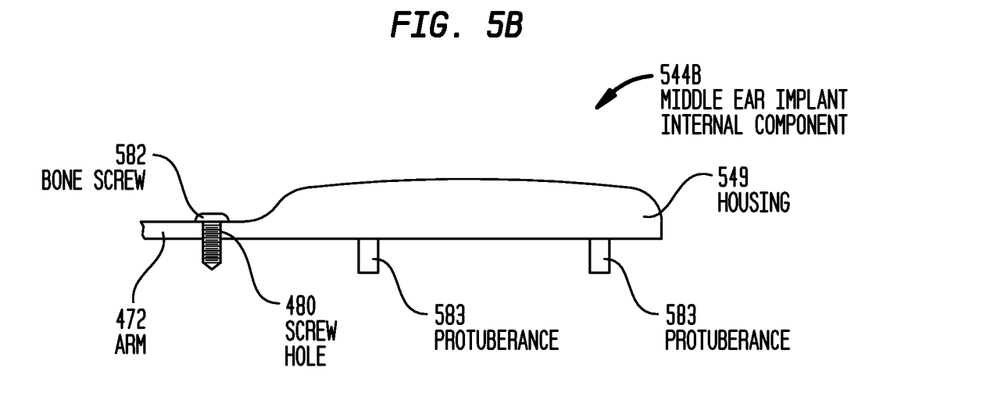
FIG. 5B depicts some details of yet another exemplary alternate embodiment of the exemplary implantable component of FIG. 3.

FIG. 5B depicts middle ear implant internal component 544B, which in some embodiments functionally corresponds to one or more or all of the middle ear implant internal components detailed herein and variations thereof. FIG. 5B depicts bone screw 582 extending through screw hole 480 in arm 472 of the actuator positioning mechanism, where the arm 472 is a monolithic component with at least a portion of housing 549. As may be seen, the middle ear implant internal component 544B further includes protuberances 583 extending downward from the bottom of housing 549. Bone screws 582 and protuberances 583, alone or in combination, correspond to bone fixation components configured to fix the middle ear implantable component 544B to bone (e.g., the skull) of a recipient. With respect to the bone screws 582, the bone screws 582 are rotatable relative to the implantable body of the middle ear implant internal component 544B so that the bone screws 582 may be screwed into the skull (either into pre-prepared holes or directly into the skull). These bone screws 582 may be configured to osseointegrate with the bone. In an exemplary embodiment, the bone screws 582 are titanium.

The protuberances 583 may also be configured to osseointegrate with the bone, although in other embodiments, the protuberances are configured to simply establish an interference fit or the like with the bone. The protuberances 583 may be fitted into pre-prepared holes in the skull, or may be configured to be forced directly into the skull (e.g., the protuberances 583 may have a relatively sharp tip and/or may be of relatively minimal thickness, etc.). In an exemplary embodiment, the protuberance(s) 583 may be located instead or in addition on the actuator positioning mechanism (e.g., on arm 472 where bone screw 582 is located at and/or adjacent thereto, etc.).

The bone screws and/or the protuberances enable the middle ear implant internal component in general and/or the actuator positioning mechanism 470 in particular, to be removably fixed to the bone.

As noted above, in an exemplary embodiment, at least a portion of the actuator positioning mechanism 470 and the implantable body of one or more or all of the middle ear implant internal components detailed herein are integral components. In an exemplary embodiment, the proximal end of the arm 472 of positioning mechanism 470 is laser welded or otherwise bonded to the housing of the implantable body. Alternatively, arm 472 of positioning mechanism 470 is an extension of the housing and is monolithic with at least a portion of the housing. By way of example, arm 472 may be formed during the same casting operation performed to cast at least a portion of the housing (e.g., the bottom portion of the housing, where a top portion of the housing is laser welded or otherwise fixed to the bottom portion of the housing). Alternatively, by way of example, arm 472 may be formed during the same stamping operation performed to form at least a portion of the housing (e.g., again, the bottom portion of the housing). In an exemplary embodiment, the housing and/or portions of the positioning mechanism are formed of titanium.

Figure 6:
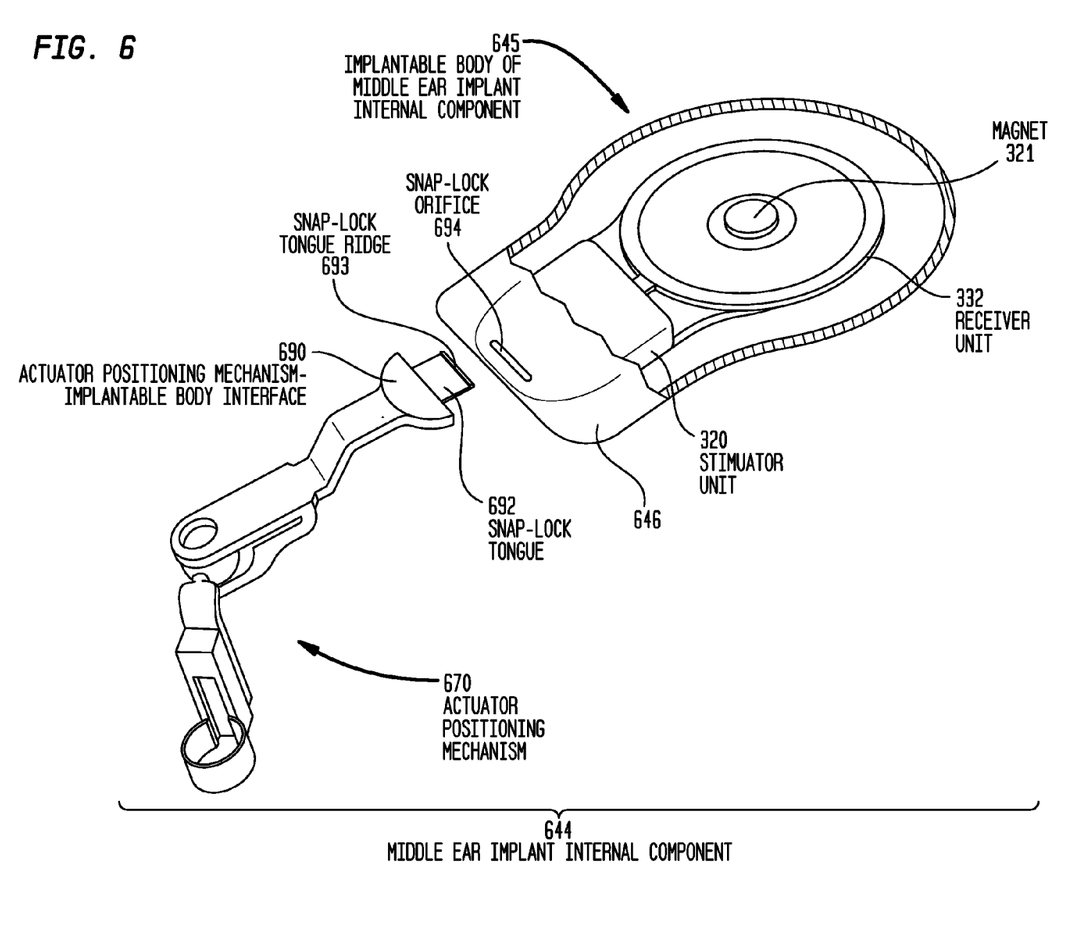
FIG. 6 depicts some details of yet another an exemplary alternate embodiment of the exemplary implantable component of FIG. 3.

FIG. 6 depicts an alternate exemplary embodiment of a middle ear implant internal component 644 that includes an actuator positioning mechanism 670 and an implantable body 645 of the internal component that are configured to be releasably fixedly attached to one another. In the embodiment of FIG. 6, actuator positioning mechanism 670 is configured to snap-lock to implantable body 645. To this end, the actuator positioning mechanism 670 includes an actuator positioning mechanism—implantable body interface 690. The interface 690 includes snap-lock tongue 692 that is configured to fit into snap-lock orifice 694 in housing 646 of the implantable body 645. As may be seen, snap-lock tongue 692 has a ridge 693 that projects upward. This ridge 693 is configured to interface with a reaction component inside the housing 646, that is not shown, to form an interference with the ridge 693. Tongue 692 is resiliently deformable such that the ridge 693 moves to snap-lock to the aforementioned reaction component inside the housing 646 to snap-lock the actuator positioning mechanism 670 to the implantable body 645. This releasably fixedly attaches the two components to one another. In an alternate embodiment, the snap-lock is configured such that the fixedly attachment obtained by the snap-lock is not releasable.

In alternate embodiments, other locking devices may be utilized to removably (or not removably) fixedly attach the actuator positioning mechanism to the implantable body. By way of example, a screw plate may be utilized. Any device, system or method that will permit the actuator positioning mechanism to be fixedly attached (removably or not) to the implantable body may be used in some embodiments detailed herein and variations thereof.

It will be understood that a sealant or the like may be applied to the interface between the actuator positioning mechanism 670 and an implantable body 645. This may be done to maintain the hermetic seal of the interior of the implantable body 645 and/or to limit or eliminate the potential for biofilm formation or a surface environment conducive to infectious bacteria growth.

As noted above, an electrical cable 328, or electrical lead, extends from the receiver-stimulator to the middle ear implant actuator. This electrical lead is configured to convey electrical impulses generated by the receiver-stimulator to the actuator 340 to actuate the actuator. In an exemplary embodiment, the electrical lead extends at least partially through structure of the actuator positioning mechanism. In an exemplary embodiment of such an embodiment, the actuator positioning mechanism functions in a manner akin to an exoskeleton relative to the electrical leads, thus protecting them from damage such as may result from impingement of a sharp object (the pressure generated by the sharp object is instead distributed to the actuator positioning mechanism, which may be more structurally robust relative to the electrical lead). Alternatively or in addition to this feature, the actuator positioning mechanism may instead prevent the electrical lead from being sharply bent.

Figure 7:
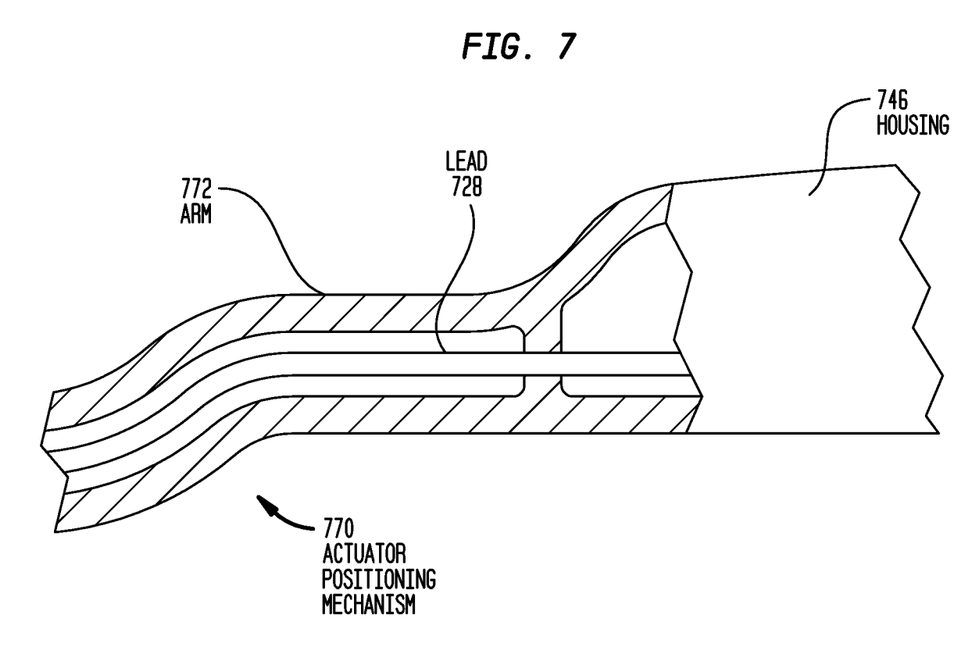
FIG. 7 depicts details of yet another exemplary alternate embodiment of the exemplary implantable component of FIG. 3.

FIG. 7 provides a cross-sectional view of a portion of an actuator positioning mechanism 740 connected to a housing 746 containing a receiver-stimulator, where an electrical lead 728 extends through the structure of the mechanism 740. Specifically, a cross-sectional view of arm 772 of the actuator positioning mechanism 740 is shown, where the arm 772 is hollow.

It is noted that while embodiments discussed above have been presented in terms of a receiver-stimulator of a hearing prosthesis being located in the housing to which the actuator positioning mechanism is attached, in other embodiments, the actuator positioning mechanism may be attached to a housing containing other functional components. By way of example, the actuator positioning mechanism may be attached to a housing that contains, or may otherwise be directly connected to, one or more or all of any of the following (including combinations thereof, such as the aforementioned receiver-stimulator): receiver, stimulator, implant battery, processor, sound processor, implantable microphone, central processing unit and memory.

Some embodiments of the present invention extend to methods of implanting an implantable component of a middle ear hearing prosthesis (or other type of prosthesis) including a functional component of the implant (e.g., receiver-stimulator, battery, etc.) and a middle ear implant actuator (or other type of actuator). Such a method is represented by flow chart 800 depicted in FIG. 8. Referring to flow chart 800, step 810 includes obtaining access to a mastoid region beneath skin of a human head. This may be done by creating a surgical incision through the skin and muscle and any other tissue between the mastoid bone of the patient/recipient of the implant and the surgeon or other medical professional creating the incision. After access is obtained, at step 820, the implantable component is fixed to the mastoid bone at a location corresponding to at least one of an outer face of the mastoid bone or a location proximate the outer face of the mastoid bone. In this regard, with reference to FIGS. 2A and 2B, the housing of the implantable body of the middle ear implant internal components detailed herein and variations thereof may be fixed to outer face of the mastoid bone 221, wherein placement of the housing corresponds to placement of stimulator unit 220 and receiver unit 232 as depicted in these figures. The outer face may be a naturally-occurring outer face of the mastoid bone, or may be an outer face established via excavating the mastoid bone to provide a recess for the housing.

Figure 8:
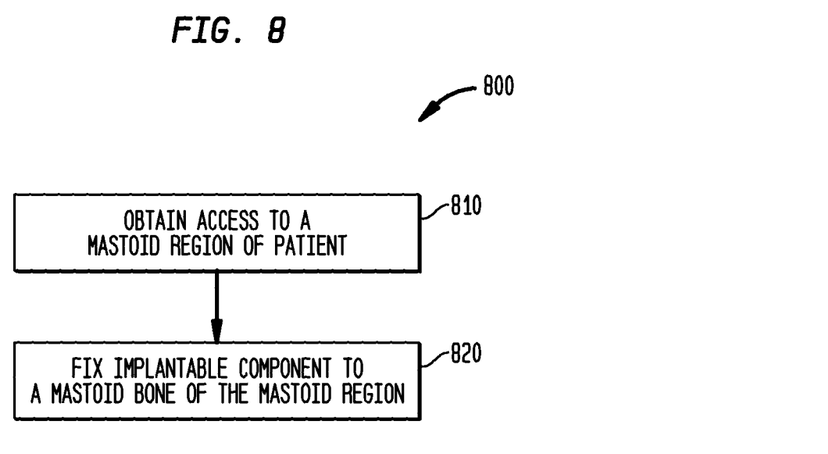
FIG. 8 depicts a simplified flow chart of a method according to an exemplary embodiment.

In the method represented by flow chart 800, the action of fixing the implantable component secures both the functional component and the middle ear implant actuator to the mastoid bone. This is accomplished, in an exemplary embodiment, due to the fact that the actuator positioning mechanism attached to the housing containing the functional component of the implantable component and the actuator positioning mechanism supports the actuator.

In an exemplary method, the action of fixing the implantable component comprises inserting one or two or more bone screws into the mastoid bone 221 at the location corresponding to at least one of the outer face of the mastoid bone or the location proximate the outer face of the mastoid bone (e.g., within the proximal portions of artificial cavity 219 with reference to FIGS. 2A and 2B). As noted above, osseointegrating protuberances may be used instead of or in addition to bone screws. Accordingly, in an exemplary method, the action of fixing the implantable component comprises inserting one or more protuberances into the mastoid bone at the location corresponding to at least one of the outer face of the mastoid bone or the location proximate the outer face of the mastoid bone.

As will be understood, some embodiments permit both the functional component of the implantable component and the middle ear implant actuator to be secured to the mastoid bone without fixing the middle ear implant actuator and structure of the implantable component proximate the middle ear implant actuator (e.g., actuator support 479 or components of the actuator support mechanism proximate the actuator, or other support components used to fix an actuator to bone) to the mastoid bone. In an exemplary embodiment, this facilitates surgical implantation of the implantable component in that all fixation actions may be performed at locations that are more readily accessible.

While various embodiments of the present invention have been described above, it should be understood that they have been presented by way of example only, and not limitation. It will be apparent to persons skilled in the relevant art that various changes in form and detail may be made therein without departing from the scope of the invention. Thus, the breadth and scope of the present invention should not be limited by any of the above-described exemplary embodiments, but should be defined only in accordance with the following claims and their equivalents.

What is claimed is:

1. An implantable component, comprising:
an implantable body configured to be fixed to a bone of a recipient, the implantable body including a functional component of an implantable medical device;
an implantable actuator positioning mechanism connected to and extending from the implantable body, the actuator positioning mechanism configured to removably receive an implantable actuator, wherein the implantable actuator positioning mechanism is configured such that a location of the implantable actuator is adjustable relative to the implantable body in at least three degrees of freedom, and
the implantable actuator, wherein the implantable actuator is removably attached to the actuator positioning mechanism, wherein a coupling element extends from the actuator, wherein an ossicles prosthesis is connected to the actuator, wherein an electrical communication cable extends from the actuator to a receiver-stimulator located in the implantable body, wherein the receiver-stimulator is the functional component.

2. The implantable component of claim 1, wherein:
the actuator positioning mechanism is configured to position the implantable actuator at an adjustably fixed location relative to the implantable body.

3. The implantable component of claim 1, wherein:
the actuator positioning mechanism includes a joint, wherein the joint comprises a malleable portion of a structural component of the implantable actuator positioning mechanism.

4. The implantable component of claim 1, wherein:
the actuator positioning mechanism includes a joint, wherein the joint is elastically deformable so as to enable an adjustment of the location of the implantable actuator relative to the implantable body in at least two degrees of freedom or more than two degrees of freedom.

5. The implantable component of claim 1, wherein:
the actuator positioning mechanism includes a joint, wherein the joint is plastically deformable so as to enable an adjustment of the location of the implantable actuator relative to the implantable body in at least two degrees of freedom or more than two degrees of freedom.

6. The implantable component of claim 1, wherein:
the actuator positioning mechanism includes a telescopic component configured to enable an adjustment of the location of the implantable actuator relative to the implantable body in a third degree of freedom.

7. The implantable component of claim 1, wherein:
at least a portion of the actuator positioning mechanism and the implantable body are integral components.

8. The implantable component of claim 1, wherein:
at least a portion of the actuator positioning mechanism and the implantable body are monolithic components.

9. The implantable component of claim 1, wherein:
the actuator positioning mechanism and the implantable body are releasably fixedly attachable to one another.

10. The implantable component of claim 1, wherein:
the functional component is a receiver-stimulator of a middle ear implant.

11. The implantable component of claim 10, wherein:
the implantable actuator positioning mechanism is rigidly connected to the implantable body.

12. The implantable component of claim 1, comprising:
the implantable actuator, wherein the implantable actuator is removably received in the actuator positioning mechanism, wherein a coupling element extends from the actuator and an electrical communication cable extends from the actuator to the functional component.

13. The implantable component of claim 1, wherein:
the implantable actuator is removably received in the actuator positioning mechanism, and the ossicles prosthesis is a stapes prosthesis.

14. The implantable component of claim 1, wherein:
the implantable actuator positioning mechanism is rigidly connected to the implantable body.

15. An implantable component, comprising:
an implantable actuator positioning mechanism configured to receive an implantable actuator, wherein the implantable actuator positioning mechanism is configured to be fixedly attached to a functional component of a hearing prosthesis, wherein
the functional component is a receiver-stimulator, and
the implantable actuator positioning mechanism is configured such that the implantable actuator, when received, is located on an opposite end of the implantable actuator positioning mechanism from a location where the implantable actuator positioning mechanism is configured to be fixedly attached to the functional component.

16. The implantable component of claim 15, wherein:
the implantable actuator positioning mechanism is configured to be removably fixedly attached to the functional component of a hearing prosthesis.

17. The implantable component of claim 15, wherein:
the implantable actuator positioning mechanism is configured to snap-lock to the functional component of the hearing prosthesis.

18. The implantable component of claim 15, wherein:
the actuator positioning mechanism includes a joint configured to enable adjustment of a location of the received actuator relative to the functional component when attached thereto in at least one degree of freedom.

19. The implantable component of claim 15, wherein:
the hearing prosthesis is configured to be fixed to a bone of a recipient;
the implantable actuator positioning mechanism is configured to removably receive an implantable actuator; and
the implantable actuator positioning mechanism is configured such that a location of the implantable actuator is adjustable relative to the functional component in at least three degrees of freedom.

20. The implantable component of claim 15, comprising:
the implantable actuator, wherein the implantable actuator is received in the actuator positioning mechanism, wherein a coupling element extends from the actuator and an electrical communication cable extends from the actuator along a trajectory that generally follows that of the implantable actuator positioning mechanism between the implantable actuator and a location where the positioning mechanism is configured to be fixedly attached to the functional component.

21. The implantable component of claim 15, comprising:
the implantable actuator, wherein the implantable actuator is received in the actuator positioning mechanism, wherein a coupling element extends from the actuator, wherein a stapes prosthesis is connected to the actuator, wherein an electrical communication cable extends from the actuator to a receiver-stimulator.

22. The implantable component of claim 15, wherein:
the implantable actuator positioning mechanism is configured to be rigidly connected to the functional component.

23. The implantable component of claim 15, wherein:
the receiver-stimulator is a receiver-stimulator of a middle ear implant.

24. The implantable component of claim 15, wherein:
the implantable actuator is a separate and different component than the functional component.

25. The implantable component of claim 15, further comprising:
the implantable actuator and the functional component, wherein the implantable actuator is a separate and different component than the functional component, and wherein the implantable actuator is received in the actuator positioning mechanism, wherein a coupling element extends from the actuator and an electrical communication cable extends from the actuator, and wherein the implantable component is fixed to a body containing the functional component.

26. An implantable component, comprising:
an implantable body, the implantable body including a receiver-stimulator; and
an implantable actuator positioning mechanism connected to and extending from the implantable body, wherein
an actuator is attached to the implantable actuator positioning mechanism, and
an electrical communications cable, separate from the implantable actuator positioning mechanism, extends from the actuator to the receiver-stimulator and connects to the implantable body on a same longitudinal side of the implantable body as the implantable actuator positioning mechanism.

27. The implantable component of claim 26, wherein:
the actuator positioning mechanism is configured to position and maintain an implantable actuator at an adjustably fixed location relative to the implantable body.

28. The implantable component of claim 26, wherein:
at least a portion of the actuator positioning mechanism and the implantable body are integral components.

29. The implantable component of claim 26, wherein:
at least a portion of the actuator positioning mechanism and the implantable body are monolithic components.

30. The implantable component of claim 26, wherein:
the receiver-stimulator is a receiver-stimulator of a middle ear implant.

31. The implantable component of claim 26, further comprising:
a cable extending from the implantable body, separate from the implantable actuator positioning mechanism.

32. An implantable component, comprising:
an implantable body, the implantable body including a receiver-stimulator of an implantable medical device hermetically sealed within the implantable body; and
a means for positioning an implantable actuator, the means for positioning an implantable actuator having means for removably receiving an implantable actuator, wherein
the means for positioning an implantable actuator is connected to and extends from the implantable body.

33. The implantable component of claim 32, wherein:
the means for positioning the implantable actuator is configured such that the implantable actuator, when received by the means for positioning the implantable actuator, is located on an opposite end of the means for positioning the implantable actuator from a location where the means for positioning the implantable actuator extends from the implantable body.

* * * * *